(12) United States Patent
Beck et al.

(10) Patent No.: US 6,840,266 B2
(45) Date of Patent: Jan. 11, 2005

(54) INTERCHANGEABLE FITTING

(75) Inventors: Bernhard Beck, Stuttgart (DE); Detlef Exner, Mönsheim (DE)

(73) Assignee: Endress & Hauser Conducta Gesellschaft fur Mess-und Regeltechnik mbH & Co., Gerlingen (DE)

( * ) Notice: Subject to any disclaimer, the term of this patent is extended or adjusted under 35 U.S.C. 154(b) by 54 days.

(21) Appl. No.: 09/985,275

(22) Filed: Nov. 2, 2001

(65) Prior Publication Data

US 2002/0083977 A1 Jul. 4, 2002

(30) Foreign Application Priority Data

Nov. 2, 2000 (DE) ........................................ 100 54 272

(51) Int. Cl.[7] .......................... G01D 21/00; G01N 1/10; G01N 17/04; F16K 51/00
(52) U.S. Cl. ....................................... 137/317; 73/866.5
(58) Field of Search ........................... 73/863.86, 866.5; 137/317

(56) References Cited

U.S. PATENT DOCUMENTS

| | | | | |
|---|---|---|---|---|
| 2,805,273 A | * | 9/1957 | Cuthbert ...................... | 137/317 |
| 3,007,340 A | * | 11/1961 | Kraftson ..................... | 73/866.5 |
| 3,576,195 A | * | 4/1971 | Richard, Jr. ................. | 137/317 |
| 3,691,846 A | * | 9/1972 | Ingold ........................ | 73/866.5 |
| 3,829,761 A | * | 8/1974 | Shimizu ..................... | 137/317 |
| 4,332,272 A | * | 6/1982 | Wendell ...................... | 137/318 |
| 4,537,071 A | * | 8/1985 | Waterman ................... | 73/866.5 |
| 4,697,465 A | * | 10/1987 | Evans et al. ................. | 73/866.5 |
| 5,174,325 A | * | 12/1992 | Okel et al. ................... | 137/317 |
| 6,338,359 B1 | * | 1/2002 | Welker ........................ | 137/317 |
| 6,357,470 B1 | * | 3/2002 | Evans et al. ................. | 137/317 |

FOREIGN PATENT DOCUMENTS

| | | |
|---|---|---|
| DE | 34 04 639 | 8/1985 |
| DE | 38 09 288 | 2/1989 |
| DE | 89 00 511.2 | 5/1989 |
| DE | 39 00 814 | 9/1989 |
| DE | 42 07 845 | 9/1993 |
| DE | 197 20 504 | 11/1998 |
| EP | 0 391 838 | 10/1990 |

* cited by examiner

*Primary Examiner*—George L. Walton
(74) *Attorney, Agent, or Firm*—Hoffman, Wasson & Gitler P.C.

(57) ABSTRACT

The invention relates to an interchangeable fitting with a fitting housing (12), a removable measurement probe (14) which is movably guided axially in the housing (12) for insertion into a container, a shut-off element (16) which closes the fitting (10) relative to the interior of the container, and a guide means (22) which can be guided to move axially in the housing (12) for holding and guiding the measurement probe (14) in the fitting housing (12) between a measurement position in which the measurement probe (14) has been inserted into the container, and a stand-by position in which the measurement probe (14) is located within the fitting housing (10), the measurement probe (14) comprising a measurement probe body (15) and a sensor (26), the measurement probe (14) being fixed with its measurement probe body (15) on the end face (23) of the guide means (22), and the sensor (26) being mounted on the free side of the measurement probe body (15) which points in the direction to the container and the cross section of the guide means (22) being smaller than the cross section of the measurement probe (14).

5 Claims, 3 Drawing Sheets

INTERCHANGEABLE FITTING

The invention relates to an interchangeable fitting with a fitting housing, a removable measurement probe which is axially guided movably in the housing for insertion into a container, a shut-off element which closes the fitting relative to the interior of the container, and a guide means which can be moved axially in the housing for holding and guiding the measurement probe in the fitting housing between a measurement position in which the measurement probe has been inserted into the container, and a stand-by position in which the measurement probe is located within the fitting housing, the measurement probe comprising a measurement probe body and a sensor.

One such interchangeable fitting can be made for measurement of the most varied quantities. In particular, measurements in fluid media, especially for pH, redox, conductivity, oxygen content and chlorine measurement can be taken with it.

For example, DE 197 20 504 discloses a device for receiving and holding a measurement electrode for taking measurements in fluid media, which comprises a housing, an inside sleeve which is supported to move axially by sliding in the housing and in which the measurement electrode is housed, the inside sleeve being movable relative to the housing such that a section of the inner sleeve which allows entry of the fluid medium into the measurement electrode tip can be moved out of the housing in order to come into contact with the liquid medium, and can be inserted again into the housing in order to clean, sterilize or calibrate the medium side of the measurement electrode or the section of the inside sleeve assigned to it, or to replace the measurement electrode by another.

These measurement probe fittings are used in immersion systems, flow systems, and add-on systems for example in analytical chemistry, in process engineering, in measurement engineering for waste water, in food chemistry, and pharmaceutical chemistry.

They are often also called seal fittings. With their housing which can likewise be made tubular like the guide means guided in them, they are located stationary on a container or tube which routes or contains the fluid process or measurement medium. In order to clean or calibrate the measurement probe the fitting need not be dismounted, but the guide means is withdrawn together with the measurement probe out of the process or measurement medium into the fitting housing and is treated there in the required manner in a cleaning or calibration chamber which is sealed against the medium side.

A corresponding fitting it likewise known from DE 2 061 978 C2 which discloses a transducer means for mounting on a container opening with a removable transducer probe, a shut-off element and a guide means which coaxially surrounds the body of the probe.

When the term container is used below, it should be understood in the most general form and should include not only vessels of any type, but also lines, channels, etc.

If at this point the measurement probe enters or is inserted into a container in which generally a process overpressure prevails, the measurement probe must be moved against the pressure. The cross section of the guide means is thus the cross section on which the process pressure acts. The higher the process overpressure, the greater the actuation forces for penetration of the measurement probe in the process which become necessary. In the conventional embodiments in which the probe diameter is for example 40 mm, as a result of the greater necessary diameter of the guide means in which the probe has been guided, in the past it was simply necessary to push the measurement probe into the container against a process pressure of 4 bar. Standard drinking water applications with 8 bar process overpressure therefore could not be managed in the past.

Therefore the object of the invention to make available an interchangeable fitting with which in high pressure applications it is possible to change the measurement probe for purposes of cleaning, sterilization and calibration, etc. during the process.

The invention achieves this object by an interchangeable fitting in which the measurement probe is fixed with its measurement probe body on the end face of the guide means and the sensor being mounted on the free side of the measurement probe body which points in the direction to the container and the cross section or the diameter of the guide means being smaller than the cross section or the diameter of the measurement probe.

The sensor can also be an integral component of the measurement probe body.

The measurement probe with its measurement probe body in this invention is no longer mounted in the guide means, i.e. is no longer coaxially surrounded by the guide means. Rather the sensor is mounted on the end face, specifically the end face of the guide means pointing in the direction to the container. In this embodiment it is no longer necessary for the cross section or the diameter of the guide means to be greater than the diameter or the cross section of the measurement probe. Thus, in this embodiment, no longer the cross section of the guide means, but the cross section of the measurement probe determines the boundary pressure up to which the sensor can be inserted into the container. In spite of a probe diameter of 40 mm, a probe can now be inserted up to 8 bar process pressure against this into the container. In this embodiment the fitting housing must be lengthened by the sensor length so that the sensor withdrawn into the stand-by position has room in this housing and the shut-off element can be closed. One such embodiment offers the advantage that the diameter or the cross section of the guide means is completely independent of the diameter or the cross section of the measurement probe.

According to a first embodiment, the fitting can have a mounting means which fixes the measurement probe in the measurement position and the stand-by position on the fitting.

It can furthermore be provided that the mounting means interacts with the shut-off element in order to prevent removal of the measurement probe when the shut-off element is opened. In particular the shut-off element can be a ball valve which is actuated by means of a handle or an actuating lever which can be swivelled from one position in the axial direction of the fitting (through position) into the position perpendicular thereto (blocked position). It can be provided that the actuating lever interacts with the actuating means of the mounting means such that it blocks the actuation means or the mounting means in its position.

The mounting means can be a tension screw union which comprises a tension unit and a screw connection unit which interacts with the tension unit, the tension unit being guided on the fitting and the tension unit and the measurement probe or the guide means can be interlocked, and by turning the screw connection unit the tension unit can be braced to the measurement probe. One such tension unit bridges any lengths of the fitting housing. After the tension screw union is loosened the tension unit releases the guide unit or the measurement probe so that the measurement probe can be removed from the fitting. It can be provided that the measurement probe or the guide means can be connected to the fitting by means of a quarter-turn fastener.

This forced control, in which with the shut-off element opened the measurement probe cannot be removed, offers the advantage that emergence of pressurized process medium is reliably prevented when the probe is removed from the process in which the fitting is being opened. The opening of the fitting with the shut-off element opened is prevented by the rotation of the tension screw union for opening the fitting being prevented by the actuating lever of the opened shut-off element. First of all, the shut-off element must always be closed by this mechanical forced control. Only then is opening of the fitting possible.

Furthermore, the interchangeable fitting on the guide means has a stop which limits the insertion depth of the measurement probe into the fitting.

Other advantages and features of the invention follow from the other application documents.

The invention will be explained below using the drawings.

Figure 1A:
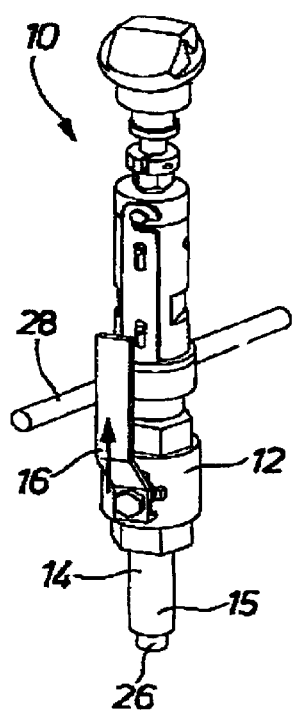
FIG. 1 shows an interchangeable fitting as claimed in the invention.
Figure 1B:
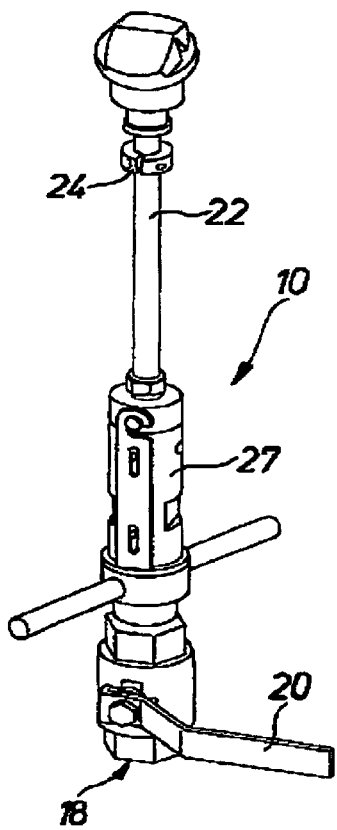
Figure 1C:
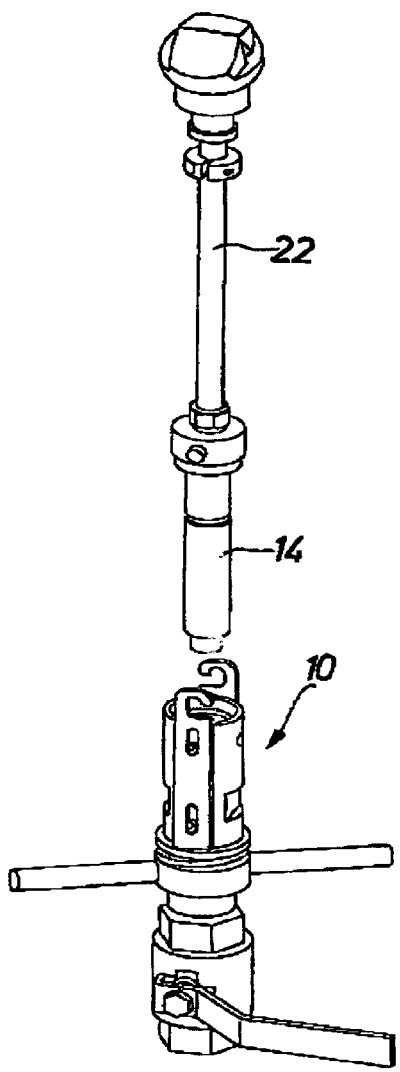

FIG. 1 shows an interchangeable fitting which is characterized in its totality by reference number 10. The interchangeable fitting 10 comprises a fitting housing 12 and a removable measurement probe 14 which is axially guided to move in the fitting housing 12 for insertion into a container which is not shown. The measurement probe 14 comprises a sensor 26 and a measurement probe body 15. On the fitting housing 12 there is a shut-off element 16 which can be transferred from the opened position as shown in representation a) into the closed position, as shown in b), and in the opened position of b) the measurement probe 14 can be pushed through an opening 18 so that the measurement probe 14 projects into the container interior. The shut-off element 16 is a ball valve with an actuating lever 20, the actuating lever 20 in the opened position running parallel to the axial direction of the interchangeable fitting 10. In the closed position the actuating lever 20 is perpendicular to it.

Representation a) shows the interchangeable fitting 10 with the measurement probe 14 in the measurement position in which the measurement probe 14 is inserted into a container, conversely the representation b) shows the standby position in which the shut-off element 16 is closed and the measurement probe 14 is withdrawn into the interchangeable fitting 10. In this position sterilization and calibration processes can be carried out. The representation c) shows the interchangeable fitting 10 with the measurement probe 14 removed. On the end of the measurement probe 14 facing away from the side of the container the probe 14 is connected to a guide means 22 which is used to guide and hold the measurement probe 14. The guide means 22 has a stop 24 which limits the insertion depth of the measurement probe 14 into the container.

Figure 3:
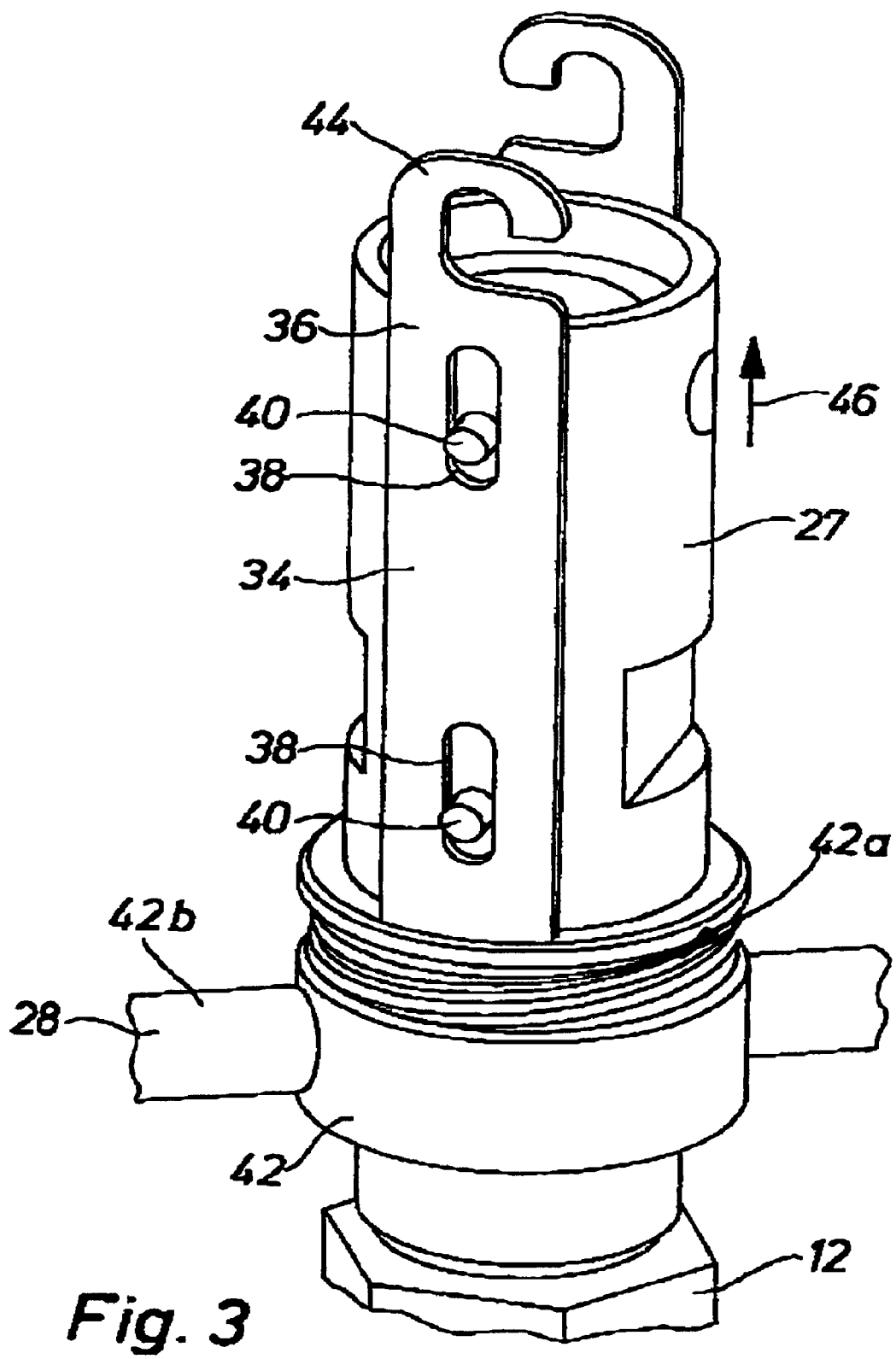

The measurement probe 4 in the interchangeable fitting 10 is fixed by means of a tension screw union 27 which is to be connected to the fitting housing 12 and which is detailed in FIG. 3.

The measurement probe 14 is located and mounted with its measurement probe body 15 on the end face of the guide means 22 so that the guide means 22 can have a smaller diameter than the measurement probe 14. The diameter of the measurement probe 14 and especially of its sensor 26 thus determines the effective area on which the process overpressure in a container acts and against which the measurement probe 14 must be pushed into the container.

For example, when using a measurement probe 14 with a diameter of 40 mm the measurement probe 14 can be pushed into a container against a pressure of 8 bar by this embodiment. These measurement probes are thus likewise well suited for example for drinking water applications.

In order to prevent removal of the measurement probe 14, as shown in c), with the shut-off element 16 opened, the actuating lever 20 of the shut-off element 16 is arranged such that in its opened position, as shown by a), it collides with the actuating means 28, specifically the handle of the tension screw union 27 which is used to fix the measurement probe 14 in the interchangeable fitting 10. I.e., the actuating handle 20 blocks the rotary motion of the tension screw union 27 by its interacting with the actuating means 28. The tension screw union 27 can thus not be opened when the shut-off element 16 is opened. Emergence of the pressurized medium from the container can thus be reliably avoided.

Figure 2A:
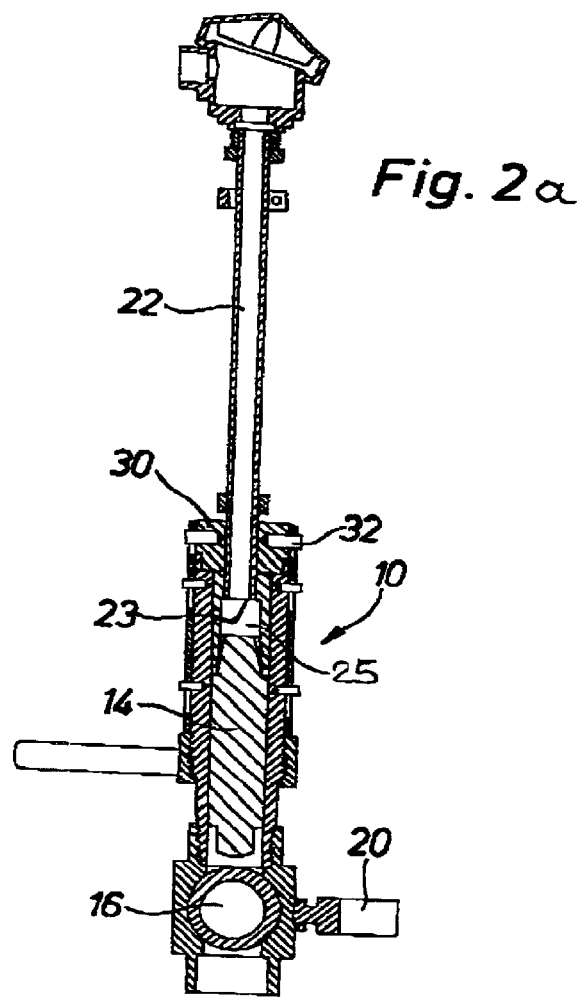
FIG. 2 shows an interchangeable fitting in a cross section in two alternatives and FIG. 3 shows a cutout from the interchangeable fitting.

FIG. 2a) shows a measurement fitting 10 as shown in FIG. 1b) in a cross section. It is apparent here that the measurement probe 14 is mounted, not as was conventional in the past in the tubular guide means 22, but is fixed on the end face 23 of the guide means 22 which points in the direction to the interior of the container. In this way the diameters of the measurement probe 14 and the guide means 22 can be decoupled so that only the diameter of the measurement probe 14 is the limiting parameter with respect to the pressure against which the measurement probe 14 can be inserted into a container. To be able to pull the measurement probe 14 fully back into the interchangeable fitting 10, the interchangeable fitting 10 can have a length which corresponds at least to the length of the measurement probe 14 in the axial direction. The shut-off element 16 is a ball valve which is shown in FIG. 2 in its closed position.

The guide means 22 above the measurement probe 14 has a mounting sleeve 30, the guide means 22 being guided to move by sliding in the mounting sleeve 30. The mounting sleeve 30 comprises two sins 32 which project radially to the outside, which are located opposite one another and which interact with the tension screw union 27 for fixing the measurement probe 14 in the interchangeable fitting 10.

Figure 2B:
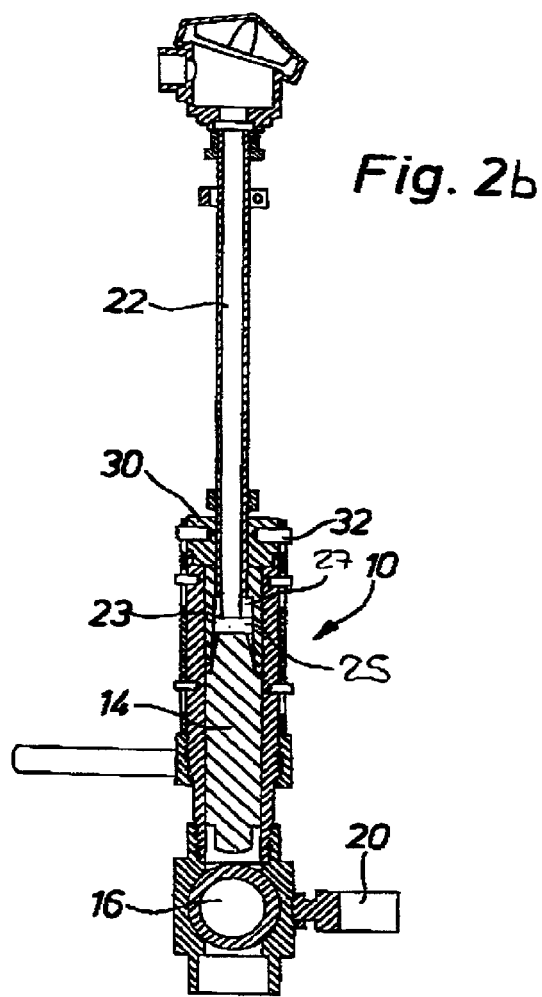

FIG. 2b shows one alterative embodiment in which the guide means 22 on its end face 23 is likewise connected to the measurement probe head 25. The latter is guided with play in the interchangeable fitting 10. In order to axially stabilize the guidance when the measurement probe 14 is moved, there is a guide ring 27 here which consists of plastic material and acts as a sliding ring. The guide ring 27 is fixed on the guide means 22 and slides along the inside wall of the interchangeable fitting 10 when the guide means 22 is moved into the measurement position. The guide ring 27 rests against the measurement probe head 25 with one side.

The wear on the components can thus be reduced.

Fixing of the measurement probe 14 by means of the tension screw union 27 will be detailed using FIG. 3. FIG. 3 shows the fitting housing 12 with the tension screw union 27. The tension screw union 27 comprises a tension unit 34 which consists of two legs 36 located on the sides opposite one another on the fitting housing 12, each of the legs 36 having two elongated holes 38 in which pins 40 which are permanently connected to the fitting housing 12 are movable guided. In this way the tension screw union 27 is axially guided during the opening and closing process.

Furthermore, the mounting means or tension screw union 27 comprises a two-part screw connection or screw connection unit 42, the part of the screw connection unit 42a which has an outside thread being securely connected to the tension unit 34. The second component of the tension means 42, 42*b* which has one inside thread and which is connected to the part 42*a* via a screw connection is connected to the actuating means 28. The tension unit 34 on its upper free end has hooks 44 into which the pin 32 of the mounting sleeve 30 can be locked by form-fit.

If at this point the screw connection unit 42 is opened, i.e. the two parts 42*a, b* are screwed apart so that the part 42*b* moves in the direction to the container side end of the fitting, the two legs 36 of the tension unit 34 move in the direction of the arrow 46 so that the measurement probe 14 is no longer braced with the interchangeable fitting 10. The pins 32 can then be removed from the hook 44 so that the quarter-turn fastener of the tension unit 34 is opened. Complete separation of the two parts 42*a, b* is not possible.

The measurement probe 14 can then be removed from the fitting housing 12.

What is claimed is:

1. An interchangeable fitting, comprising a fitting housing,
   a removable measurement probe which is movably guided axially in the housing for insertion into a container,
   a shut-off element which closes the fitting relative to the interior of the container, and
   a guide means which can be guided to move axially in the housing for holding and guiding the measurement probe in the fitting housing between a measurement position in which the measurement probe has been inserted into the container, and a stand-by position in which the measurement probe is located within the fitting housing,
   the measurement probe comprising a measurement probe body and a sensor, wherein the measurement probe is fixed with its measurement probe body on the end face of the guide means, the sensor being mounted on the free side of the measurement probe body which points in the direction to the container and the cross section of the guide means being smaller than the cross section of the measurement probe
   wherein the fitting has a mounting means which fixes the measurement probe in the measurement position and the stand-by position on the fitting, the mounting means interacts with the shut-off element in order to prevent removal of the measurement probe when the shut-off element is opened, the mounting means comprises a tension screw union which comprises a tension unit and a screw connection unit, the tension unit being guided on the fitting and the tension unit and the measurement probe or the guide means can be interlocked, and by turning the screw connection unit the tension unit can be braced with the measurement probe or the guide means.

2. The interchangeable fitting as claimed in claim 1, wherein the shut-off element has an actuating lever which blocks the actuating means of the mounting means in its position with the shut-off element opened.

3. The interchangeable fitting as claimed in claim 1, wherein the measurement probe or the guide means can be connected to the tension screw union by means of a quarter-turn fastener.

4. The interchangeable fitting as claimed in claim 1, wherein the guide means comprises a stop which limits the insertion depth of the measurement probe into the fitting.

5. The interchangeable fitting as claimed in claim 1, wherein the guide means is surrounded by a guide ring which is guided to be able to move by sliding in the interchangeable fitting and which stabilizes the guide means axially in the interchangeable fitting.

* * * * *